US007182964B2

(12) United States Patent
Kupper et al.

(10) Patent No.: US 7,182,964 B2
(45) Date of Patent: Feb. 27, 2007

(54) DISSOLVING THIN FILM XANTHONE SUPPLEMENT

(75) Inventors: Roman Kupper, Erlanger, KY (US); Marlene Smothers, Erlanger, KY (US)

(73) Assignee: DBC, LLC, Lehi, UT (US)

( * ) Notice: Subject to any disclaimer, the term of this patent is extended or adjusted under 35 U.S.C. 154(b) by 0 days.

(21) Appl. No.: 10/987,439

(22) Filed: Nov. 12, 2004

(65) Prior Publication Data

US 2005/0191336 A1 Sep. 1, 2005

Related U.S. Application Data

(60) Provisional application No. 60/519,852, filed on Nov. 13, 2003.

(51) Int. Cl.
*A01N 65/00* (2006.01)
*A01N 43/16* (2006.01)
*A61K 9/70* (2006.01)
*A61K 47/00* (2006.01)
*A61F 13/00* (2006.01)

(52) U.S. Cl. ............... 424/777; 424/435; 424/439; 424/443; 514/453; 514/455

(58) Field of Classification Search ............... 424/777, 424/443, 439, 435, 58, 49, 449, 725, 769; 514/453, 455; 549/394, 392
See application file for complete search history.

(56) References Cited

U.S. PATENT DOCUMENTS

| 4,592,913 | A | | 6/1986 | Hara |
| 5,554,286 | A | * | 9/1996 | Okamoto et al. |
| 6,159,512 | A | | 12/2000 | Reyes |
| 6,177,096 | B1 | * | 1/2001 | Zerbe et al. |
| 6,231,866 | B1 | | 5/2001 | Mann |
| 6,419,903 | B1 | * | 7/2002 | Xu et al. |
| 6,455,057 | B1 | | 9/2002 | Barrett et al. |
| 6,596,298 | B2 | * | 7/2003 | Leung et al. |
| 6,730,333 | B1 | * | 5/2004 | Garrity et al. |
| 2003/0138467 | A1 | * | 7/2003 | Ptchelintsev |
| 2003/0206942 | A1 | * | 11/2003 | Kulkarni et al. |

FOREIGN PATENT DOCUMENTS

| EP | 000496349 A1 | * | 1/1992 |
| JP | 02009817 A | * | 1/1990 |
| JP | 8-208501 | | 8/1996 |
| JP | 9-110688 | | 4/1997 |
| JP | 11-43442 | | 2/1999 |
| JP | 2001247469 A | * | 9/2001 |

OTHER PUBLICATIONS

Nilar, L.J.H. Phytochemistry (2002), 60: 541-548. Xanthones from the heartwood of Garcinia mangostana.*
Suksamrarn, S. et al. Journal of Natural Products (2002), 65(5): 761-763. Xanthones from the green fruit hulls of Garcinia mangostana.*
International Search Report and Written Opinion of the International Searching Authority, Sep. 14, 2005.
Alternative Styles, Jun. 1, 2001, pp. 1-5, Beverage Industry Communications, Inc., ISSN: 0148-6187, vol. 92, Issue 6, 2001 WL 14821362.
Bates, R.P., et al., Principles and practices of small- and medium-scale fruit juice processing, FAO Agricultural Services Bulletin 146, Rome (2001).
Bennett, Graham J. et al., Xanthones from Guttiferae, Review Article No. 43, Department of Chemistry, National University of Singapore, Singapore (1988).
Caius, J. F., The Medicinal and Poisonous Plants of India, pp. 430-431, Scientific Publishers, India, (1986).
Campbell, R.J., South American Fruits Deserving Further Attention, p. 431-439, In: J. Janick (ed.), Progress in new crops. ASHS Press, Arlington, VA (1996).
Chairungsrilerd, N, et al., Pharmacological Properties of α-mangostin, a Novel Histamine $H_1$ Receptor Antagonist, European Journal of Pharmacology, 314 pp. 351-356 (1996).
Chairungsrilerd, et al., Mangostanol, A Prenyl Xanthone from *Garcinia mangostana*, 43 Phytochemistry No. 5, pp. 1099-1102 (1996).
Chairungsrilerd, et al., Histaminergic and Serotonergic Receptor Blocking Substances from the Medicinal Plant *Garcinia mangostana*, 62 Planta Medica, pp. 471-472 (1996).
Chairungsrilerd, Nattaya, et al., γ-Mangostin, a Novel Type of 5-Hydroxytryptamine 2A Receptor Antagonist, Naunym-Schmiedeberg's Arch Pharmacol, 357:25-31 (1998).
Chairungsrilerd, Nattaya, et al., Effect of γ-mangostin through the inhibition of 5-hydroxy-tryptamine$_{2A}$ receptors in 5-fluoro-x-methyltryptamine-induced head-twitch response of mice, British Journal of Pharmacology, 123, 856-862 (1998).

(Continued)

*Primary Examiner*—Michele Flood
(74) *Attorney, Agent, or Firm*—McAndrews, Held & Malloy, Ltd.

(57) ABSTRACT

A nutraceutical composition containing xanthones for oral ingestion is disclosed. The composition is a rapidly dissolving film comprising water soluble polymers and xanthones. The xanthones are, preferably, derived from natural plant sources, especially from fruit of *Garcinia mangostana* L. plant.

9 Claims, No Drawings

OTHER PUBLICATIONS

Chanarat, P., et al., Immunopharmacological Activity of Polysaccharide from the Pericarp of Mangosteen Garcinia: Phagocytic Intracellular Killing Activities, 80 Supp. 1 J. Med. Assoc. Thai., S149-54 (Sep. 1997).

Chen, et al., Active Constituents Against HIV-1 Protease from *Garcinia mangostana*, 62 Plant Medica, pp. 381-382 (1996).

Chen, M., Fruity Way to Good Health, Oct. 1, 2000, 3 pages, Sunday Mail, Malaysia, WL 2959378 (2000).

Clusiacaea, Calophyllum inophyllum L., pp. 214-218.

Dahanukar, et al., Pharmacology of Medicinal Plants and Natural Products, Indian Journal of Pharmacology, p. S96 (2000).

Dictionary entry for "Garcinia cambogia", p. 327.

Dictionary or Encyclopedia entry for "Garcinia L. Gulliferae", p. 1050.

Du, etal., A Research Note—Anthocyanins of Mangosteen,Garcinia Mangostana, 42 Journal of Food Science No. 6, pp. 1667-1668 (1977).

Duke, et al., CRC Handbook of Alternative Cash Crops, pp. 257-259, CRC Press (1993).

Fairchild, D., The Mangosteen, The Journal of Heredity, pp. 339-347.

Frankfurt and Leipzig, Garcinia, Mangostan Tree, Botantical Encyclopedia, 1773, 3 pages, Fourth Edition.

Furukawa, K., et al., Novel Types of Receptor Antagonist from the Medicinal Plant Garcinia Mangostana, Nippon Yakurigaku Zasshi, 110 Supp. 1:153-1158 (Feb. 1998).

Furukawa, K. et al., The Mode of Inhibitory Action of Alpha-Mangostin, A Novel Inhibitor, on the Sarcoplasmic Reticulum Ca (2+)-Pumping ATPase from Rabbit Skeletal Muscle, 71(4) JP J. Pharmacol., 337-40 (Aug. 1996).

Garcin, Laurentius, The Settling of a new Genus of Plans, called after the Malayans, Mangostans, Translated from the French by Mr. Zollman, F.R.S.

Garcinia Mangostana Linn: Mangostan, e-mail attachment, 1 page.

Gatorade Thirst Quencher—Sabor de Mangosteen, Sep. 6, 1999, 1 page, International Product Alert, ISSN: 1086-1238; vol. 16, Issue 17, 1999 WL 23229526.

Going to Extremes, Jul. 11, 1996, 2 pages, Gorman's New Product News, vol. 32, No. 6, ISSN: 1048-020X, 1996 WL 9833883.

Gopalakrishnan, G., et al., Evaluation of the Antifungal Activity of Natural Xanthones from Garcinia Mangostana and Their Synthetic Derivatives, J. Nat. Prod. 1997, 60, 519-524.

Greey, M, Vietnamese Give Drinks a Twist, Oct. 5, 1988, 3 pages, The Toronto Star, 1988 WL 5710363.

Hanes, P., Zesty Treats on Malaysian Streets Once Mainly Fish and Rice, Today's Fare Has a Mix of Flavors, Mostly from China and India, Oct. 24, 1991, 3 pages, Christian Science Monitor, 1991 WL 5363325.

Ho, C.K., Huang, Y.L., Chen, C.C., Garcinone E, a xanthone derivative, has potent cytotoxic effect against Hepatocellular carcinoma cell lines, 2 pages, Planta Med, 68(11): 975-79, 2002.

Holleran, J., The Zotics Splash, Jun. 1, 2000, 7 pages, Beverage Industry, 2000 WL 18770402.

Hope, J., Mice Can Help Men to Become Fathers, Claims Fertility Doctor, 33/17/99, 2 pages, Daily Mail 6, 1999 WL 12913860.

Iinuma, M., et al., Antibacterial Activity of Xanthones from Guttiferaeous Plants Against Methicillin-Resistant Staphylococcus Aureus, 48(8) J. Pharm. Pharmacol. 861-5 (Aug. 1996).

Jardin, Kisantu, Le Jardin Botanique de Kisantu, printed from an e-mail on Aug. 3, 2004, 4 pages.

Jinsart, et al., Inhibition of Wheat Embryo Calcium-Dependent Protein Kinase and Other Kinases by Mangostin and γ-Mangostin, 31 Phytochemistry No. 11, pp. 3711-3713 (1992).

Kader, P., et al., Involvement of Blueberry Peroxidase in the Mechanisms of Anthocyanin Degradation in Blueberry Juice, Journal of Food Science, 2002, vol. 67, No. 3, Institute of Food Technologists.

Kirtikar, et al., Indian Medicinal Plants, pp. 261-262, International Book Distributors, 2nd edition, India (1999).

Likhitwitayawuld, K., et al., Antimalarial Xanthones from Garcinia Cowa, Planta Med. 1998, 64, 70-72.

Mahabusarakam et al., Antimicrobial Activities of Chemical Constitutents from *Garcinia mangostana* Linn, 12 J. Sci. Soc. Thailand, pp. 239-242 (1986).I.

Mahabusarakam et al., Inhibition of Lipoprotein Oxidation by Prenylated Xanthones Derived from Mangostin, 33 Free Rad. Res., pp. 643-659 (2000).

Maronia, H. et al., Pharmacological Properties of Some Aminoalkanolic Derivatives of Xanthone, Pharmazie, vol. 56, pp. 567-572, 2001.

Matsumoto, K., et al., Induction of Apoptosis by Xanthones from Mangosteen in Human Lukemia Cell Lines, J. Nat. Prod. 2003, 66, 1124-1127.

Mistic Zotics Beverage—Yuzu; Pitaya; Acerola Berry; Mangosteen; Marula, Apr. 24, 2000, 1 page, International Product Alert, ISSN: 0740-3801; vol. 30, Issue 8, 2000 WL 9202590.

Mokhtar N., Research to Diversify Use of Farm Products, Nov. 12, 1996, 3 pages, Business Times, Malaysia 02, 1996 WL 14216524.

Moongkarndi P, et al., Antiproliferation, Antioxidation and Induction of Apoptosis by Gardinia Mangostana (Mangosteen) on SKBR3 Human Breast Cancer Cell Line, J. Ethnopharmacol. Jan. 2004, 90(1):161-6, Pub Med search results, Department of Microbiology, Bangkok, Thailand.

Morton, J., Mangosteen, In: Fruits of Warm Climates, 1987, pp. 301-304, Miami, FL.

Morton, J. F., Major Medicinal Plants, Botany, Culture and Uses, 1977, pp. 1-12, Charles C. Thomas, Publisher, Springfield, Illinois.

Nakatani, Keigo, et al., Inhibition of Histamine Release and Prostaglandin $E_2$ Synthesis by γ-Mangostine, A Thai Medicinal Plant, Biol. Pharm. Bull., Sep. 2002, 1137-41, 25(9), Pharmaceutical Society of Japan.

Nakatani, Keigo, et al., Inhibition of Cyclooxygenase and Prostaglandin $E_2$ Synthesis by γ-Mangostin, A Xanthone Derivative in Mangosteen, in C6 Rat Glioma Cells, 63 Biochemical Pharmacology, pp. 73-79 (2002).

New Products Blur the Lines, Mar. 1, 2001, pp. 1-4, Beverage Industry Communications, Inc., ISSN: 0148-6187, vol. 92, Issue 3, 2001 WL 14820975.

New Products Flavored with Orange, The Milwaukee Journal Sentinel, May 10, 2000, 2000 WL 3857627.

Okudaira, C., et al., Inhibition of Acidic Sphingomyelinase by Xanthone Compounds Isolated From Garcinia Speciosa, J. Enzyme Inhibition, 2000, vol. 15, pp. 129-138.

Paull, R.E., et al., Mangosteen, 3 pages, Department of Tropical Plant and Soil Sciences, University of Hawaii at Manoa, Honolulu, HI and Department of Horticulture, Kasetsart University, Bangkok, Thailand.

Peres, Valdir et al., Review, Tetraoxygenated Naturall Occurring Xanthones, Phytochemistry, vol. 55, pp. 683-710, 2000.

Perry, L. M., et al., Medicinal Plants of East and Southeast Asia, 5 pages and 174-175, 1980, The MIT Press, Cambridge, Massachusetts and London, England.

Plengmaneepun, S., Alcoholic Drinks: 'Grapes-Only' Rule Limits Opportunities, Aug. 13, 1999, 2 pages, Bankok Post, 1999 WL 22710031.

Requested Recipe: Mangosteen Wine, The Winemaking Home Page, 2 pages, 2002.

Settheetham, W., and Ishida, T., Study of Genotoxic Effects of Antidiarrheal Medicinal Herbs on Human Cells in Vitro, Southeast Asian J. Trop Med Public Health, 26 Supp. 1:306-310 (1995).

Shankaranarayan, et al., Pharmacological Profile of Mangostin and Its Derivatives, 239 int. Pharmacodyn, pp. 257-269, India (1979).

Shankaranarayan, et al., Effect of Mangostin, a Xanthone from *Garcinia mangostana* Linn. In Immunopathological and Inflammation Reactions, 18 Indian Journal of Experimental Biology, pp. 843-846 (1980).

Siddappa and Bhatie, Preservation of Mangosteen (Garcinia Mangostana L.), Bull. Centr. Food Res. Inst. Mysore, India 3:296-97 (1954).

Suksamrarn, S., et al., Xanthones from the Green Fruit Hulls of Garcinia Mangostana, Journal of Natural Products, 2002, pp. 761-763, vol. 65, No. 5, American Chemical Society and American Society of Pharmacognosy.

Sundaram, B.M., et al., Antimicrobial Activities of Garcinia Mangostana, Short Communications, pp. 59-60, 1983.

Sunkist Tropical Drink—Mangosteen, Nov. 3, 1997, 1 page, International Product Alert, vol. 14, No. 21 ISSN: 1086-1238, 1997 WL 12715299.

Sunkist World Fruits Puali Fruit Water—California Orange; Mediterranean Blend, Sep. 7, 1998, 1 page, International Product Alert, vol. 15, No. 17, ISSN: 1086-1238, 1998 WL 14765678.

Templeman, J.F., Nuevo Suplemento Natural Impacta Comunidad Medica, La prensa Su Salad web site, printed from an e-mail on Aug. 3, 2004.

Thai Medicinal Plants—Recommended for Primary Health Care System, pp. 160-162, Norman Farnsworth edition, Medicinal Plant Information Center, Thailand (1992).

Toops, D., IFT's Primary Theme—Wellness; But There Were Plenty of Surprises, Aug. 1, 2002, 6 pages, Food Processing Publishing Co., 2002 WL 14439138.

Torquay De-Lite Low Joule Natural Mineral Water—Apple, Plum & Blackcurrant; Lemon, Lime & Orange; Orange and Mangosteen; Peach and Cherimoya; Pink Grapefruit, Lemon & Mandarin, Nov. 6, 1999, 2 pages, International Product Alert, ISSN: 1086-1238; vol. 17, Issue 21, 1999 WL 31465706.

Torquay Reef Soft Drink—Lemon with a hint of Raspberry; Lemonade with a Twist of Lime; Organe with a Splash of Mangosteen; Tropical with a Splice of Cherimoya and Passionfruit, Nov. 6, 1999, 2 pages, International Product Alert, ISSN 1086-1238; vol. 17, Issue 21, 1999 WL 31465707.

Truly Top Quality, Apr. 19, 2001, 3 pages, The Statesman, Ltd., Asia Intelligence Wire, 2001 WL 19354465.

Will Wellness Trend Live On? (Panel Discussion), Oct. 1, 2001, 6 pages, Beverage Industry 48, ISSN 0148-6187, vol. 92, Issue 10, 2001 WL 29298168.

Williams, Peta, et al., Mangostin Inhibits the Oxidative Modification of Human Low Density Lipoprotein, pp. 175-183 University of Western Australia, Department of Medicine at Royal Perth Hospital, Australia Faculty of Science, Prince of Songkla University, Thailand (1994).

www.worldagroforestry.org—Agroforestree Database, Garcinia mangostana, 6 website pages.

www.commercial-directory.com—diagnosispro/page1.htm, Toxicity Ratings for Herbals (From Planet-RX, PDR for Herbal Medicines, the AphA Practical Guide to Herbal Therapies, and H. Winter Griffith MD Guide and Many Other Sources, 2 pages.

www.foodmarketexchange.com—web page showing "Mangosteen wine ready to make debut."

www.hkbic.bch.cuhk.edu.hk—herbalLiteratureOnline/allHerbalData.html, Record No. 67.

www.ibiblio.org/herbmed/eclectic/kings—garcinia-mang.html, King's American Dispensatory: Gardinia, printed from the Web on Apr. 29, 2002.

www.mistic.com—web page showing "Mistic Zotics—Thailand Mangosteen Fruit."

Yaacob, et al., Mangosteen Cultivation, Plant Production and Protection Paper, pp. 10-13 (Food and Agriculture Organization of the United Nations) (1995).

www.larsoncenturyranch.com—web pages featuring "The Origins of XanGo: Southeast Asia."

www.mangoxan.com—web pages featuring You've Just Discovered MangoXan™! Now, Discover What MangoXan™ Can Do For You!.

* cited by examiner

DISSOLVING THIN FILM XANTHONE SUPPLEMENT

RELATED APPLICATIONS

This application is a non-provisional utility patent application claiming priority to U.S. provisional patent application Ser. No. 60/519,852, filed Nov. 13, 2003, now pending. The entire specification of the provisional application referred to above are hereby incorporated by reference to provide continuity of disclosure.

FIELD OF THE INVENTION

The presently described technology relates to a nutraceutical composition for use in the oral cavity that contains xanthones. More particularly, the presently described technology relates to a rapidly dissolving film for oral ingestion comprising xanthones, for example, derived from fruit of the *Garcinia mangostana* L. plant.

BACKGROUND OF THE INVENTION

Rapidly dissolving thin films for oral ingestion are well-known in the art. These films are a recognized alternative to pills, tablets, liquids and other forms of consumable therapeutic or cosmetic substances. These thin films offer several advantages over prior art forms. They are compact and easily carried about, usually via a plastic case having a pliable hinge that allows repeated opening and closing. They are also capable of being ingested discretely, as opposed to ingestion of pills or tablets that generally require movement of the mouth or jaws.

Further advantages of thin films for oral ingestion are explained in detail in U.S. Pat. No. 6,177,096, which is incorporated herein by reference, U.S. Pat. No. 6,419,903, which is incorporated herein by reference, and U.S. patent application No. 2003/0206942, which is also incorporated herein by reference. These references further disclose the general chemistry and technology associated with thin films and various methods of manufacturing them.

It is also generally known in the art that rapidly dissolving films can be used for delivering therapeutic amounts of pharmaceutically active ingredients and cosmetically active ingredients. For example, as disclosed in U.S. Pat. No. 6,177,096, thin films can be used to deliver cosmetic agents such as breath freshening compounds, flavors for oral hygiene, fragrances for oral hygiene, active ingredients for oral cleansing and active ingredients for dental cleansing, as well as drugs such as hypnotics, sedatives, antiepileptics, antispasodics, diuretics, antitussive expectorants and antibiotics.

The medicinal properties of the *Garcinia mangostana* L. plant have increasingly been the subject of recent pharmacological and clinical studies. These studies have shown that some of the natural compounds derived from the plant yield surprising medicinal benefits, especially the xanthone compounds. The history of the *Garcinia mangostana* L. plant and the pharmacological benefits of individual xanthone compounds is described in more particular detail in U.S. Pat. No. 6,730,333 (Garrity et al.), which is incorporated herein by reference.

Despite the known use of rapidly dissolving films for oral ingestion and the documented medicinal benefits of natural xanthones, the combination of these two distinct fields has been heretofore unknown. Accordingly, there exists a need in the art for a rapidly dissolving film material comprising xanthones suitable for oral ingestion. Moreover, there is a need in the art for a simple method of delivering therapeutic amounts of xanthones. There is a further need in the art for a xanthone product that can be easily and unobtrusively consumed. There exists a further need in the art for a consumable xanthone product that comprises xanthones derived from the fruit of the *Garcinia mangostana* L. plant, otherwise known as the mangosteen plant.

BRIEF SUMMARY OF THE INVENTION

The present technology described herein uniquely provides a source of natural xanthones that can be easily transported and inconspicuously consumed. In particular, the presently described technology relates to a rapidly dissolving film for oral ingestion comprising xanthones.

In one aspect, the presently described technology provides orally consumable film composition comprising at least one ingredient selected from the group consisting of saliva inducing agents, surfactants, stabilizing agents, emulsifiers, thickeners, plasticizers, antimicrobials, water, water soluble polymers, binders, polyethylene oxides, propylene glycols, sweeteners, flavor enhancers, colorants, polyalcohols, and combinations thereof; and at least one xanthone.

Preferably, xanthones to be used in the presently described technology are derived from natural plant sources, especially from fruit of *Garcinia mangostana* L. plant. For example, the pericarp of the fruit of *Garcinia mangostana* L. plant can be used alone or in combination with the pulp of the fruit as an excellent source of xanthones.

BRIEF DESCRIPTION OF SEVERAL VIEWS OF THE DRAWINGS

Not Applicable

DETAILED DESCRIPTION OF THE INVENTION

It is understood that the terminology used herein is used for the purpose of describing particular embodiments only, and is not intended to limit the scope of the presently described technology. It is also understood that, as used herein and in the appended claims, the singular forms "a," "an," and "the" include plural reference, unless the context clearly dictates otherwise.

Unless defined otherwise, all technical and scientific terms used herein have the same meanings as commonly understood by one of ordinary skill in the art to which this invention belongs. While various methods, compositions, and materials of the presently described technology are described herein, any methods and materials similar or equivalent to those described herein can by used in the practice or testing of the presently described technology. All references cited herein are incorporated by reference in their entirety.

The film, which is normally a thin film, of the presently described technology is instantly wettable and rapidly dissolving. Thus, the film adheres to the roof of one's mouth or tongue, quickly and totally dissolves. The film comprises xanthone compounds for delivery through oral consumption.

In one embodiment of the invention, the xanthones are derived from natural plant sources. Preferably, the xanthones can be derived from fruit of the *Garcinia mangostana* L. plant. In one preferred embodiment of the presently described technology, the xanthones are derived from the pericarp of mangosteen fruit. In another preferred embodiment, the xanthones are derived from a mixture of mangosteen fruit pulp and pericarp, thus ensuring a natural, holistic source of xanthones.

In addition to xanthone compounds, the film of the presently described technology can comprise one or more of the following ingredients: saliva inducing agents, surfactants, stabilizing agents, emulsifiers, thickeners, plasticizers, antimicrobials, water, water soluble polymers, binders, polyethylene oxides, propylene glycols, sweeteners, flavor enhancers, colorants and polyalcohols.

Any number of saliva enhancing agents can be used in the presently described technology. These agents are well known in the art, which include common food-grade sweeteners such as glucose, dextrose, fructose, lactose, maltose, xylose, sucrose, corn sugar syrup, and other sweet mono- or di-saccharides. A combination of synthetic sweeteners plus a non-sugar, sugar-related compound such as sorbitol, hexitol, maltitol, xylitol, and mannitol, or starch hydrolysate such as Lycansin, or the like is also advantageous in the presently described technology. Aspartame may also be used.

The surfactants that may be used in the presently described technology can vary, but generally compromise one or more anionic surfactants. For example, when a combination of surfactants is used, the first component may be a polyoxyethylene alkyl ether and the second component may be a polyoxyethylene sorbitan fatty acid ester. The ether compound may have an HLB value of 14–16, while the ester compound may have an HLB value of between 10 and 20. Of course, these values can vary, as one of ordinary skill in the art will appreciate.

Stabilizers useful in the presently described technology include xanthan gums, carrageenan, and the like. In one embodiment of the presently described technology, antimicrobials are included in the formulation. These compounds include essential oils such as eucalyptol, menthol, vacrol, thymol, methyl salicylate, verbenone, eugenol, gerianol and combinations thereof.

The water soluble polymers of the presently described technology can exhibit film forming properties, so the xanthone-containing mixture can be spread into a thin film with sufficient tensile strength to withstand cutting, dicing and packaging of the product. Typical polymers include, but are note limited to, amylase, arabic gum, carboxymethyl cellulose, carboxyvinyl polymers, collagen, dextrin, gluten, guar gum, acacia gum, high amylase starch, hydroxyethyl cellulose, hydroxypropyl cellulose, hydroxypropylated high amylase starch, hydroxypropylmethyl cellulose, methylmethacrylate copolymers, polyacrylic acid, polyethylene glycol, polyvinyl alcohol, polyvinyl pyrrolidone, pullulan, sodium alginate, tragacanth gum, whey protein isolate, and combinations thereof.

Polyalcohols give a soft feel to the film and allow the film to conform to the contours of the oral cavity. Useful polyalcohols for purposes of the presently described technology include glycerol, polyethylene glycol, propylene glycol, glycerol monoesters with fatty acids or other known polyalcohols. If colorants are used in the presently described technology, they should be non-toxic and approved by the Food and Drug Administration.

Although there are a number of different methods of producing the thin films of the presently described technology, one method is as follows: The non-water soluble plasticizers, surfactants, and polyalcohols are dissolved in an appropriate amount of solvent, which may include water-alcohol mixtures. The other water soluble ingredients and xanthones are then slowly added until a single homogeneous solution is obtained. It may be necessary to heat the solution to accommodate thorough mixture and dissolving of all ingredients. The resulting soup mixture is then poured or coated onto a non-stick drying surface that allows even spreading of the mixture across its surface. The mixture is slowly cooled and/or dried until it hardens and the thin film is formed. The thin films are then cut into shapes suitable for packing.

The invention will now be explained with reference to the following example, which are given for illustration only and are not intended to be limiting thereof.

EXAMPLE 1

A rapidly dissolving thin film was made by combining the ingredients listed below:

| Ingredients | Amount |
| --- | --- |
| Natural compounded liquid mangosteen flavor | 4.5%–4.9% |
| Mangosteen fruit extract | 0.1%–0.5% |
| Vitamin C | 0.2% |
| Aspartame | 0.04% |
| Xanthan gums | 2%–3% |
| Water | Remainder |

In this example, whole fruit of the mangosteen fruit is ground into a mixture containing pericarp and fruit pulp. Xanthones are then extracted from the mangosteen whole fruit mixture by dissolving the whole fruit mixture in an alcohol based solvent. The solvent containing extracted xanthones is then mixed with other ingredients in the amount of from about 0.1% to about 0.5% to make a mixture solution. The mixture solution is rolled out on a sheet, and water is evaporated off using an airflow cooling tunnel over a period of about 24 hours. The resulted thin film is then cut into desired shapes and sizes.

The presently described technology may be embodied in other specific forms without departing from its spirit or essential characteristics. The described embodiments are to be considered in all respects only as illustrative and not restrictive. The scope of the presently described technology is, therefore, indicated by the appended claims rather than by the foregoing description. All changes that come within the meaning and range of equivalency of the claims are to be embraced within their scope.

What is claimed is:

1. An orally consumable film composition comprising:
   at least one saliva inducing agent;
   at least one ingredient selected from the group consisting of surfactants, stabilizing agents, emulsifiers, thickeners, plasticizers, antimicrobials, water, water soluble polymers, binders, polyethylene oxides, propylene glycols, sweeteners, flavor enhancers, colorants, polyalcohols, and combinations thereof; and
   xanthones derived from a mixture of pulp and pericarp of fruit of Garcinia mangostana L. plant.

2. The film composition of claim 1, wherein the is xanthones are derived from fruit of Garcinia mangostana L. plant by a process comprising:
   grinding whole fruit of Garcinia mangostana L. plant into a mixture of pericarp and fruit pulp; and
   extracting xanthones from the mixture.

3. The film composition of claim 1, wherein the water soluble polymers are selected from the group consisting of amylose, arabic gum, carboxymethyl cellulose, carboxyvinyl polymers, collagen, dextrin, gluten, guar gum, acacia gum, high amylose starch, hydroxyethyl cellulose, hydroxypropyl cellulose, hydroxypropylated high amylose starch, hydroxypropylmethyl cellulose, methylmethacrylate copolymers, polyacrylic acid, polyethylene glycol, polyvinyl alcohol, polyvinyl pyrrolidone, pullulan, sodium alginate, tragacanth gum, whey protein isolate, and combinations thereof.

4. The film composition of claim 1, wherein the at least one saliva inducing agent is selected from the group consisting of glucose, dextrose, fructose, lactose, maltose, xylose, sucrose, corn sugar syrup, sorbitol, hexitol, maltilol, xylitol, mannitol, starch hydrolysate, aspartame and combinations thereof.

5. The film composition of claim 1, wherein the surfactants comprise one or more anionic surfactants.

6. The film composition of claim 1, wherein the stabilizing agents are selected from the group consisting of xanthan gums, carrageenan, antimicrobials, and combinations thereof.

7. The film composition of claim 6, wherein the antimicrobials comprising one or more essential oils.

8. The film composition of claim 7, wherein the one or more essential oils are selected from the group consisting of eucalyptol, menthol, vacrol, thymol, methyl salicylate, verbenone, eugenol, gerianol and combinations thereof.

9. The film composition of claim 1, wherein the polyalcohols are selected from the group consisting of glycerol, polyethylene glycol, propylene glycol, glycerol monoesters with fatty acids, and combinations thereof.

* * * * *